United States Patent
Chakfe et al.

(10) Patent No.: US 10,004,616 B2
(45) Date of Patent: Jun. 26, 2018

(54) TREATMENT KIT, TREATMENT DEVICE, AND ASSOCIATED METHOD OF PRODUCTION

(71) Applicants: UNIVERSITE DE STRASBOURG, Strasbourg (FR); NIVERSITE DE HAUTE ALSACE, Mulhouse (FR); HOPITAUX UNIVERSITAIRES DE STRASBOURG (HUS), Strasbourg (FR)

(72) Inventors: Nabil Chakfe, Hindisheim (FR); Bernard Durand, Pfastatt (FR); Coralie Marchand, Mulhouse (FR)

(73) Assignees: UNIVERSITE DE STRASBOURG, Strasbourg (FR); UNIVERSITE DE HAUTE ALSACE, Mulhouse (FR); HOPITAUX UNIVERSITAIRES DE STRASBOURG, Strasbourg (FR)

( * ) Notice: Subject to any disclaimer, the term of this patent is extended or adjusted under 35 U.S.C. 154(b) by 0 days. days.

(21) Appl. No.: 14/426,800

(22) PCT Filed: Sep. 11, 2013

(86) PCT No.: PCT/EP2013/068834
§ 371 (c)(1),
(2) Date: Mar. 9, 2015

(87) PCT Pub. No.: WO2014/041028
PCT Pub. Date: Mar. 20, 2014

(65) Prior Publication Data
US 2015/0216686 A1 Aug. 6, 2015

(30) Foreign Application Priority Data
Sep. 11, 2012 (FR) .................................. 12 58524

(51) Int. Cl.
A61F 2/856 (2013.01)
A61F 2/07 (2013.01)
A61F 2/06 (2013.01)

(52) U.S. Cl.
CPC ................ *A61F 2/856* (2013.01); *A61F 2/07* (2013.01); *A61F 2/064* (2013.01);
(Continued)

(58) Field of Classification Search
CPC .. A61F 2/07; A61F 2/064; A61F 2/856; A61F 2002/061; A61F 2002/067; A61F 2250/006; A61F 2250/0062
See application file for complete search history.

(56) References Cited

U.S. PATENT DOCUMENTS

| 6,013,854 A | * | 1/2000 | Moriuchi | A61F 2/91 606/194 |
| 6,585,762 B1 | | 7/2003 | Stanish | |

(Continued)

FOREIGN PATENT DOCUMENTS

| EP | 1 836 995 A1 | 9/2007 |
| EP | 1 847 237 A1 | 10/2007 |

(Continued)

OTHER PUBLICATIONS

International Search Report, dated Nov. 5, 2013, from corresponding PCT application.

*Primary Examiner* — Dinah Baria
(74) *Attorney, Agent, or Firm* — Young & Thompson

(57) ABSTRACT

The kit includes: a first implant (16) defining a window (26), and a second implant (18) including a second tubular body (42) designed to be positioned in the window (26). The second implant (18) includes a retaining member for retaining the second implant (18) relative to the first implant. The kit further includes a retaining ring (20) for retaining the (Continued)

second implant (18) attached on the first tubular body (22) in the window (26) and delimiting an insertion passage (60) for the second implant (18). The retaining ring (20) is elastically deformable in the window (26) to allow a reversible increase of at least 20%, advantageously at least 30%, of the outer contour of the insertion passage (60).

15 Claims, 10 Drawing Sheets

(52) U.S. Cl.
CPC ... *A61F 2002/061* (2013.01); *A61F 2002/067* (2013.01); *A61F 2240/002* (2013.01); *A61F 2250/006* (2013.01); *A61F 2250/0062* (2013.01); *Y10T 29/49826* (2015.01)

(56) References Cited

U.S. PATENT DOCUMENTS

| | | | |
|---|---|---|---|
| 8,808,351 B2 * | 8/2014 | Osborne | A61F 2/07 623/1.13 |
| 2005/0102021 A1 * | 5/2005 | Osborne | A61F 2/07 623/1.13 |
| 2006/0155359 A1 | 7/2006 | Watson | |

FOREIGN PATENT DOCUMENTS

| | | |
|---|---|---|
| WO | 2005/034808 A1 | 4/2005 |
| WO | 2005/034810 A1 | 4/2005 |
| WO | 2011/051812 A1 | 5/2011 |

\* cited by examiner

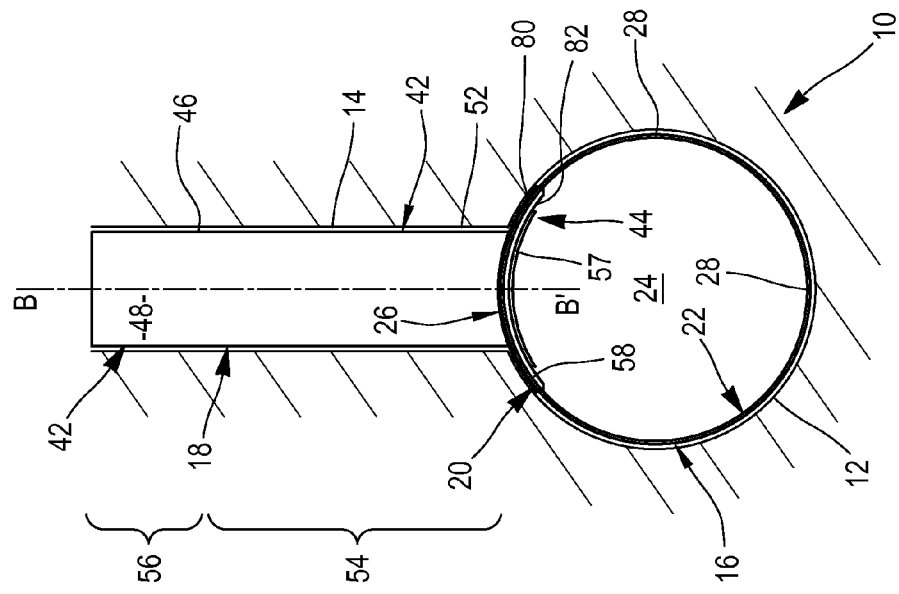
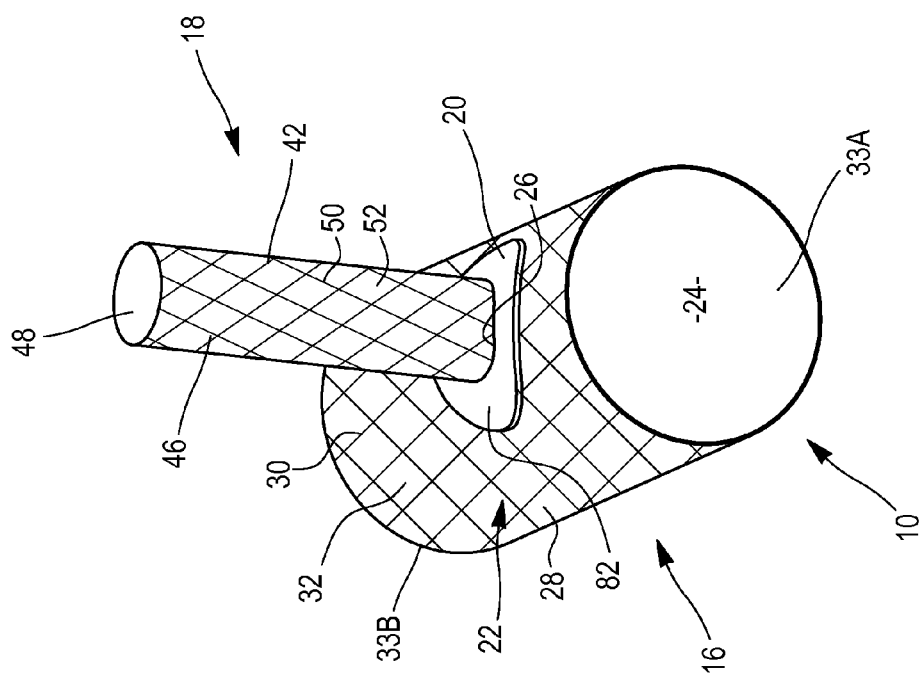

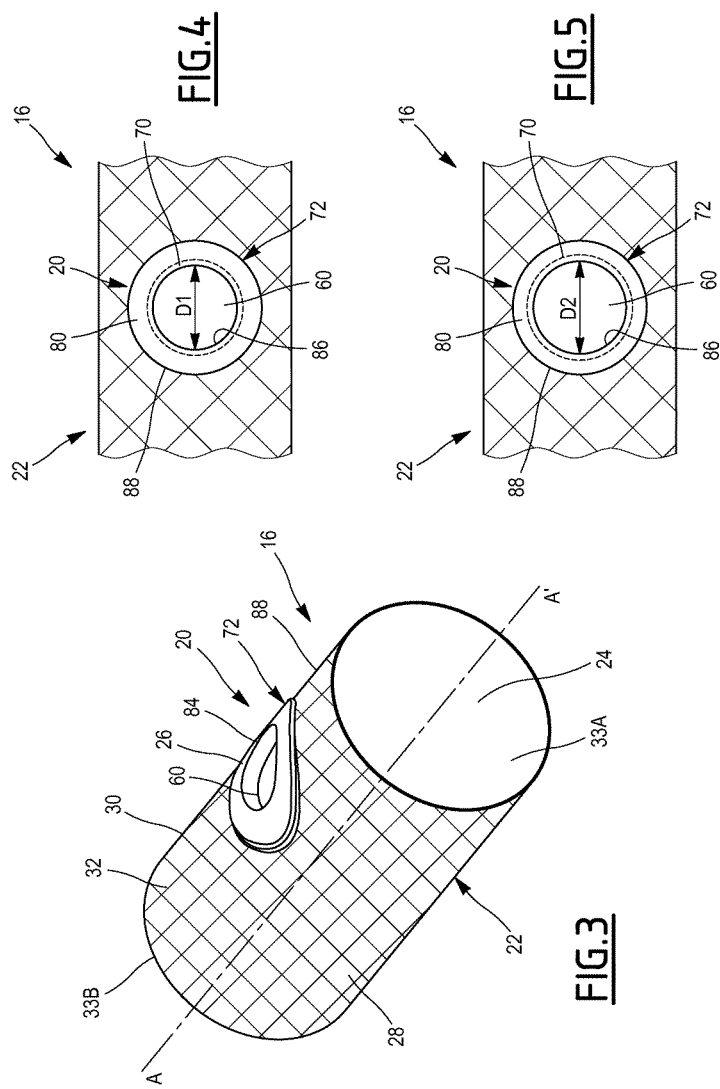

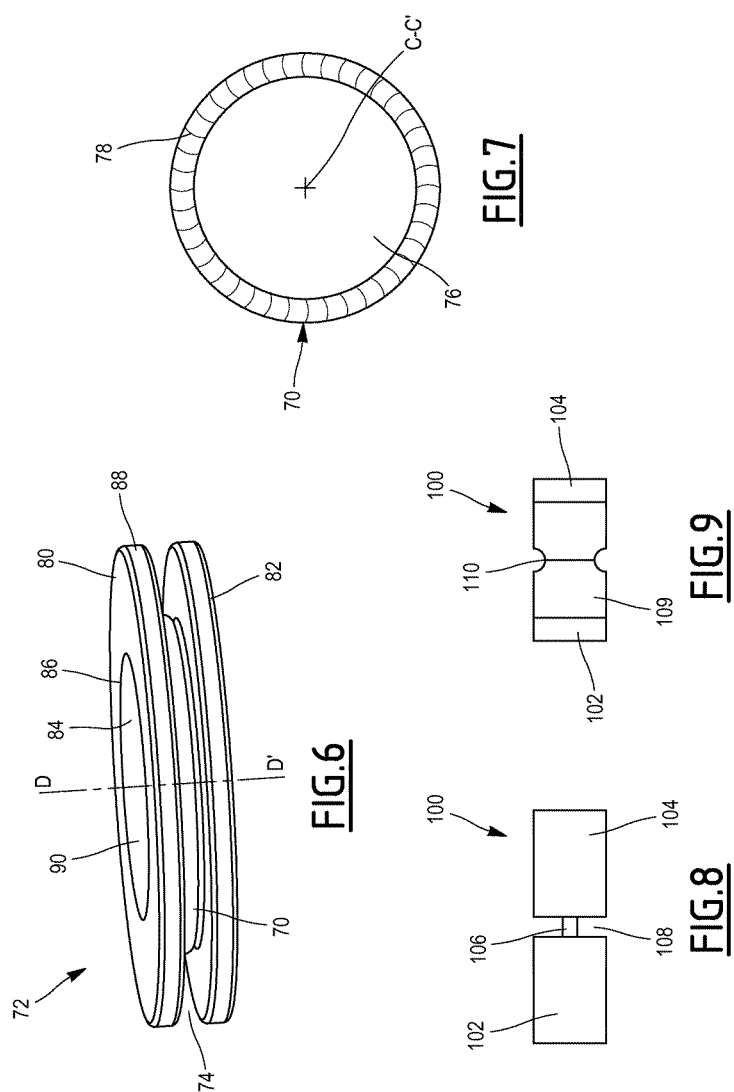

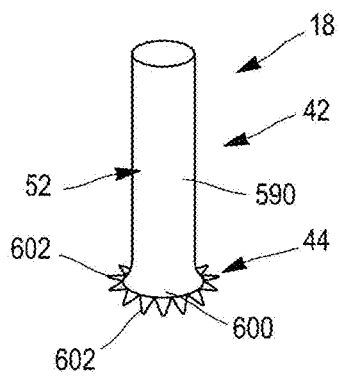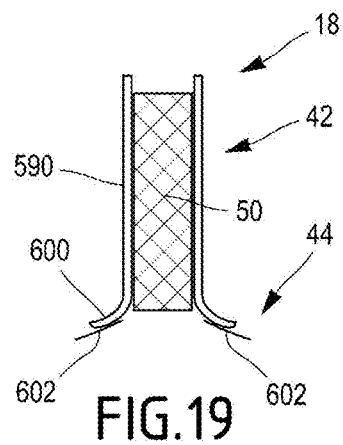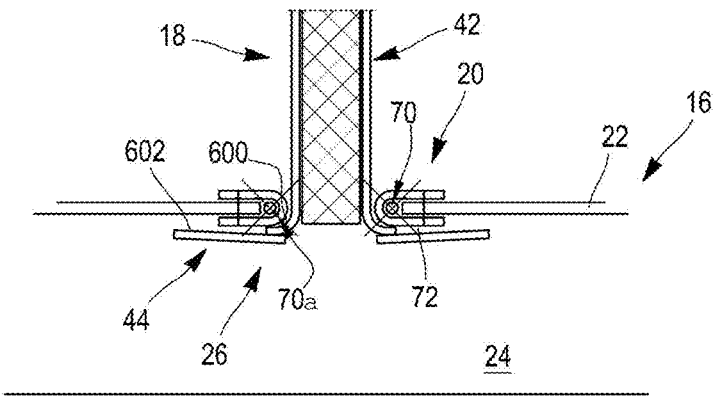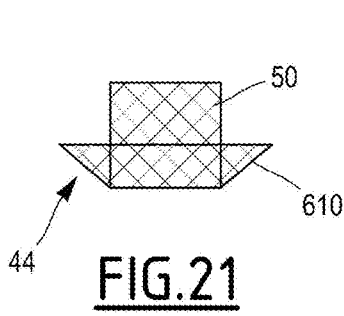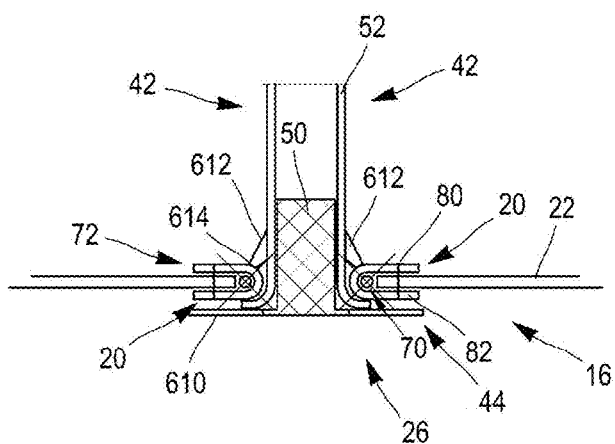

TREATMENT KIT, TREATMENT DEVICE, AND ASSOCIATED METHOD OF PRODUCTION

BACKGROUND OF THE INVENTION

The present invention relates to a treatment kit comprising:
- a first implant comprising a first tubular body defining a window
- a second implant comprising a second tubular body designed to be positioned in the window of the first tubular body to protrude relative to the first implant, the second implant comprising a retaining member retaining the second implant relative to the first implant;
- a ring for retaining the second implant assembled on the first tubular body in the window and delimiting an insertion passage for the second implant.

Such a kit is for example designed to be implanted in a cavity of a living being comprising a first conduit, and at least one branch protruding transversely from the first conduit. The cavity is for example a conduit for the circulation of a bodily fluid, such as a blood flow conduit.

In one example, the blood flow conduit is the aorta, in which a first implant is implanted. A second implant is deployed in an artery branched on the aorta, such as the iliac artery, the renal artery, the superior mesenteric artery, the coeliac artery and the supra-aortic arterial trunks, etc.

Alternatively, the first implant is designed to be positioned in the aortic arch. The second implant is then placed in one of the branches emerging in the aortic arch, such as the left common carotid artery, the left subclavian artery or the brachiocephalic arterial trunk.

Other applications are possible in the venous system, in particular in the inferior vena cava at the iliac bifurcation, at the anastomosis of the renal veins and the superior vena cava, at the anastomosis of its collateral branches.

Such a kit is generally implanted in a blood flow conduit to treat zones having defects or diseases, such as aneurysms or dissections.

In order to implant the kit, endoluminal techniques are currently preferred when they can be done. Indeed, these techniques are less invasive for the patient and reduce the mortality and morbidity levels, as well as the hospital stay time.

The endoluminal techniques provide excellent results to treat lesions in the descending thoracic aorta, which is linear. However, in the case of the aortic arch, implanting the kit using the endoluminal route presents some difficulties.

First, the first implant must be flexible enough to be able to adapt to the tortuosity of the arterial tree and curve to be brought into the aortic arch in a satisfactory manner, then deployed while conforming to the anatomy of that vessel.

Next, several secondary implants must be mounted transversely through windows arranged in the first implant. The role of these second implants is to fasten the first implant axially while avoiding the risk of migration, and to cover the supra-aortic arterial branches in order to ensure revascularization of those branches.

In order to deploy a kit as described above in a blood flow conduit having a branch, it is first known to release the first implant in the blood flow conduit. A window arranged in the first implant is positioned across from the source of each branch in which a second implant must be implanted. Then, the second implant is introduced into the window of the first implant through the branch.

The second implant is next deployed and is fixed on the first implant via at least one retaining member. The retaining member is for example a collar that can be radially deployed at one end of the second implant.

To ensure proper operation of the kit once it is implanted in the body, it is necessary to produce quasi-total sealing between the inner contour of the window arranged in the first implant and the outer contour of the second implant.

To that end, US 2006/0155359 describes a kit of the aforementioned type, in which the second implant comprises, at its end connected to the first implant, a double collar delimiting an annular throttle making it possible to receive the outer wall of the first implant. In this patent, the sealing is produced by the collars on the inner and outer faces of the main endoprosthesis by pressing the surfaces against one another.

Such a kit improves the sealing between the first implant and the second implant, in particular when the second implant is substantially perpendicular to the first implant.

However, in certain anatomical configurations, the second implant is inclined relative to a local axis of the first implant at the window, and is therefore not perpendicular to the axis. Furthermore, in some cases, the outer contour of the second implant is not conjugated with the inner contour of the window. The sealing between the first implant and the second implant cannot be done completely, which may lead to complications for the patient.

SUMMARY OF THE INVENTION

One aim of the invention is therefore to obtain a treatment kit comprising a first implant, and a second implant implanted in a window of the first implant, in which sealing is provided between the first implant and the second implant, irrespective of the position or configuration of the second implant relative to the first implant.

To that end, the invention relates to a kit of the aforementioned type, characterized in that the retaining ring is elastically deformable in the window to allow a reversible increase of at least 20%, advantageously at least 30%, of the outer contour of the insertion passage.

The kit according to the invention may comprise one or more of the following features, considered alone or according to any technically possible combination(s):
- the second implant is movable relative to the first implant between an idle position spaced away from the window and an active position implanted in the window, the retaining ring being elastically deformed when the second body is positioned in the window, the inner contour of the insertion passage having a shape conjugated with the outer contour of the second body situated in contact with the retaining ring;
- the retaining ring comprises an envelop assembled on the first body around the window, the envelop defining a housing extending at least partially around the window, the retaining ring comprising an elastic member, in particular a spring positioned in the housing, the elastic member advantageously having an annular shape;
- the elastic member is a helical spring, advantageously closed on itself, the helical spring delimiting a central opening;
- the envelop comprises a first collar fastened on an outer surface of the first body, a second collar fastened on an inner surface of the first body and a circumferential wall connecting the first collar to the second collar, the housing being delimited between the first collar, the second collar and the circumferential wall, the spring
extending around the circumferential wall;
the retaining member of the second implant is formed by
a deployable radial collar;
the second implant is auto-expandable between a retracted
configuration and a deployed configuration constituting
its idle configuration;
the first body is a tubular endoprosthesis, the second body
being a tubular endoprosthesis;
the first tubular body delimits a central passage extending
along a longitudinal axis between a first axial opening
and a second axial opening, the window being a lateral
window emerging transversely relative to the longitu-
dinal axis between the axial openings;
the first tubular body delimits a central passage extending
along a longitudinal axis between a first axial opening
and a second axial opening, the window being defined
by one of the axial openings;
the second implant comprises at least one outside wedg-
ing element, advantageously a wedging tab, protruding
from the second tubular body toward the retaining
member, the retaining member and the outer wedging
member defining an intermediate space between them
for gripping the retaining ring;
the retaining member comprises a frustoconical skirt
folded toward the second tubular body.
The invention also relates to a kit comprising:
a first implant, the first implant comprising a first tubular
body defining a window;
a second implant comprising a second tubular body
designed to be positioned in the window of the first
tubular body to protrude relative to the first implant, the
second implant comprising a retaining member for
retaining the second implant relative to the first
implant;
a retaining ring for retaining the second implant attached
on the first tubular body in the window and delimiting
an insertion passage for the second implant,
characterized in that the retaining ring comprises an
envelop assembled on the first body around the window, the
envelop defining a housing extending at least partially
around the window, the retaining ring comprising an elastic
member, in particular a spring positioned in the housing, the
elastic member advantageously having an annular shape.
The kit according to the invention does not necessarily
comprise the characteristic whereby the retaining ring is
elastically deformable in the window to allow a reversible
increase of at least 20%, advantageously of at least 30%, of
the outer contour of the insertion passage.
The kit according to the invention may comprise one or
more of the features defined above.
The invention also relates to a treatment device compris-
ing a first implant comprising a first tubular body defining a
window, and a retaining ring for retaining a second implant,
assembled to the window and delimiting an insertion pas-
sage for the second implant, characterized in that the retain-
ing ring is elastically deformable in the window to allow a
reversible increase of at least 20%, advantageously at least
30%, of the outer contour of the insertion passage.
The device according to the invention may comprise one
or more of the following features, considered alone or
according to any technically possible combination(s):
the retaining ring comprises an envelop assembled on the
first body around the window, the envelop defining a
housing extending at least partially around the window,
the retaining ring comprising an elastic member, in
particular a spring positioned in the housing, the elastic
member advantageously having an annular shape.
the elastic member is a helical spring, advantageously
closed on itself, the helical spring delimiting a central
opening;
the first tubular body delimits a central passage extending
along a longitudinal axis between a first axial opening
and a second axial opening, the window being a lateral
window emerging transversely relative to the longitu-
dinal axis between the axial openings.

The invention also relates to a treatment device compris-
ing a first implant comprising a first tubular body defining a
window, and a retaining ring for retaining a second implant,
assembled in the window and delimiting an insertion pas-
sage of the second implant,
characterized in that the retaining ring comprises an
envelop assembled on the first body around the window, the
envelop defining a housing extending at least partially
around the window, the retaining ring comprising an elastic
member, in particular a spring positioned in the housing, the
elastic member advantageously having an annular shape.

The device according to the invention does not necessar-
ily comprise the feature according to which the retaining
ring is elastically deformable in the window to allow a
reversible increase of at least 20%, advantageously at least
30%, of the outer contour of the insertion passage.

The device according to the invention may comprise one
or more of the features defined above.

The invention also relates to a method for manufacturing
a device, characterized in that it comprises the following
steps:
providing a first implant comprising a first tubular body
defining a window;
fastening a retaining ring of the second implant in the
window, the retaining ring delimiting an insertion pas-
sage for a second implant, characterized in that the
retaining ring is elastically deformable in the window
to allow a reversible increase of at least 20%, advan-
tageously at least 30%, of the outer contour of the
insertion passage.

The method according to the invention may comprise one
or more of the following features, considered alone or
according to any technically possible combination(s):
it comprises a step for manufacturing the retaining ring,
the manufacturing step comprising providing an
envelop defining a housing, and placing an elastic
member, in particular a spring, in the housing of the
envelop, the step for fastening the retaining ring com-
prising fastening the envelop on the first body;
the step for fastening the envelop comprises fastening a
first collar on an outer surface of the first body, fasten-
ing a second collar on an inner surface of the first body
and providing a circumferential wall connecting the
first collar to the second collar, the housing being
delimited between the first collar, the second collar and
the circumferential wall, the elastic member being
positioned around the circumferential wall;
it comprises a step for manufacturing the envelop com-
prising:
forming a tube, advantageously from cloth;
creating a throttle in the tube;
freezing the throttle in the tube to form the housing.

BRIEF DESCRIPTION OF THE DRAWINGS

The invention will be better understood upon reading the
following description, provided solely as an example, and in
reference to the appended drawings, in which:

FIG. 1 is a three-quarters front perspective view of a first kit according to the invention, in which the first implant has been mounted in the second implant;

FIG. 2 is a view, in section along a transverse plane, of the kit of FIG. 1;

FIG. 3 is a perspective view of the first implant of FIG. 1;

FIG. 4 is a top view of the implant of FIG. 3, the retaining ring occupying an idle configuration;

FIG. 5 is a view similar to FIG. 4, the retaining ring occupying an expanded configuration;

FIG. 6 is a partial perspective view of the retaining ring;

FIG. 7 is a top view of the spring positioned in the retaining ring;

FIG. 8 is a schematic view of a device designed to manufacture the ring of FIG. 6;

FIG. 9 is a view similar to FIG. 8 during the manufacture of the ring;

FIG. 18 illustrates an alternative of a second implant that may be positioned in a first implant according to the invention;

FIG. 19 shows a partial section of the implant of FIG. 18;

FIG. 20 illustrates the implant of FIG. 18 positioned in the first implant;

FIG. 21 illustrates an example framework for another alternative of the second implant;

FIG. 22 is a view similar to FIG. 20 of the other alternative of the second implant.

DETAILED DESCRIPTION OF THE PREFERRED EMBODIMENTS

Figure 10:
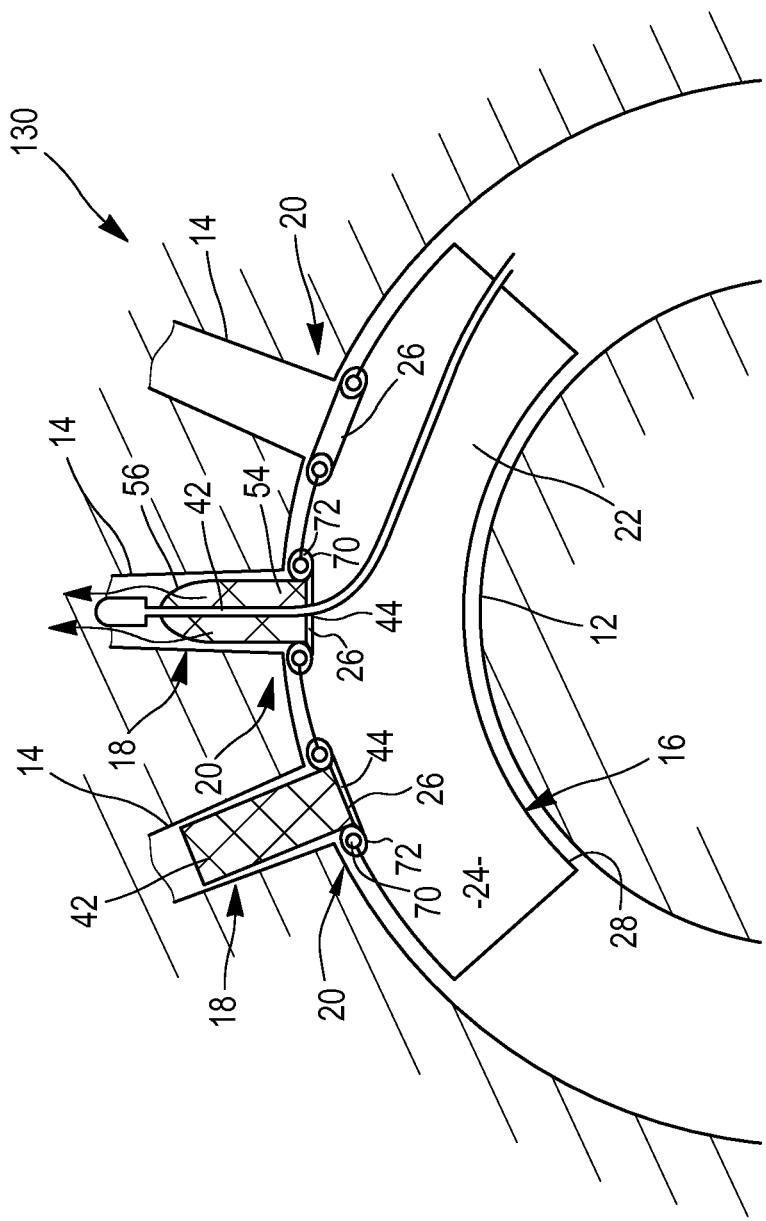
FIG. 10 is a schematic partial sectional view of a second kit according to the invention, during implantation in a bent blood flow conduit, in one possible example of catheterization from the inside of the main endoprosthesis.

A first kit 10 according to the invention is illustrated by FIGS. 1 to 7. The first kit 10 is designed to be implanted in an inner cavity defined in the body of a human being or animal.

In reference to FIG. 2, the cavity comprises a main tubular segment 12 and a branch 14 emerging in the main segment 12.

The main segment 12 and the branch 14 are for example blood flow conduits in the vascular system of a human being or animal. The main segment 12 is for example an artery or a vein, and the branch 14 is a blood flow conduit emerging in the artery or vein.

In particular, the segment 12 can be the aorta, in particular at the aortic arch, or a linear segment of the aorta in which segments of abdominal endoprostheses are connected.

As illustrated by FIGS. 1 and 2, the kit 10 comprises a first implant 16 designed to be implanted in the main segment 12, and a second implant 18. In this example, the second implant 18 is designed to be assembled transversely on the first implant 16 to protrude from the first implant 16 in the branch 14.

According to the invention, the kit 10 further comprises an elastic ring 20, mounted on the first implant 16 to produce sealing around the second implant 18.

In reference to FIG. 3, the first implant 16 comprises a first tubular body 22 defining a central passage 24 for the flow of a bodily fluid and a lateral window 26 for insertion of the second implant 18 opening into the central passage 24.

The tubular body 22 has a tubular shape with central axis A-A'. It comprises a tubular wall 28 advantageously formed by an openwork frame 30 covered by a coating layer 32.

The framework 30 is for example formed from at least one elastic wire, for example made from shape memory metal, such as Nitinol, or polymer.

The or each wire is for example configured in a zigzag or in the form of a trellis defining meshes.

The coating layer 32 closes off the intermediate openings defined between the wire segments. It sealably delimits the central passage 24 over the entire length of the body 22, with the exception of the window 26.

The coating layer 32 is for example formed with a base of a liquid-tight film, for example having a thickness smaller than 1 mm.

The film is for example made from a silicone polymer, or a fluorinated polymer such as PTFE.

The central passage 24 is sealably delimited by the peripheral wall 28. It emerges axially on either side of the tubular body 22 by a proximal opening 33A and a distal opening 33B. It emerges transversely through the window 26.

The window 26 is arranged transversely in the peripheral wall away from the openings 33A, 33B.

The first implant 16 is deployable between a contracted configuration bringing it toward its implantation location (not shown) and an expanded implantation configuration.

In the contracted configuration, the implant 16 is radially contracted toward the axis A-A' and has a minimal radial expanse, so that it can be inserted into the main segment 12.

In the expanded configuration, it has a maximal diameter.

In one advantageous embodiment, the first implant 16 is auto-expandable. It is then spontaneously deployed from its contracted configuration to its expanded configuration, its expanded configuration constituting its idle configuration.

As illustrated by FIGS. 1 and 2, the second implant 18 comprises a second tubular body 42 and at least one radial member 44 for retaining the second implant 18 in the first implant 16.

The second tubular body 42 comprises a tubular wall 46 defining an auxiliary central passage 48.

As for the tubular wall 28 of the first body 22, the tubular wall 46 of the second body 42 comprises an openwork frame 50 covered by a coating layer 52. The frame 50 is for example formed by at least one wire configured in a zigzag, or by a trellis of wires defining meshes.

In the example illustrated in FIG. 2, the coating layer 52 covers the first proximal region 54 of the tubular body 42 situated in contact with the retaining member 44 to make that first region 54 liquid-tight.

However, at least one distal region 56 situated opposite the retaining member 44 is exposed so as to allow the passage of liquid. This ensures vascularization of the branch 14 during implantation of the second implant 18.

In the example shown in FIG. 2, the radial retaining member 44 protrudes radially from a proximal edge of the second tubular body 42. In this example, the radial member 44 is formed by a collar 58 protruding radially relative to an axis B-B' of the second tubular body 42.

The collar 58 is for example continuous over the entire periphery of the distal edge 57 around the axis B-B'. Alternatively, the collar 58 is formed by a plurality of discontinuous disjointed fingers.

The radial member 44 thus protrudes radially around the axis B-B' relative to the second tubular body 42, advantageously perpendicular relative to the axis B-B'.

Once the second implant 18 is mounted on the first implant 16, the radial member 44 is pressed against an inner surface of the first tubular body 22 situated around the window 26 to prevent the radial outward movement of the second implant 18 relative to the first implant 16.

The second implant 18 is thus generally T-shaped and is referred to as a "T-stent".

Examples of second implants 18 are described in patent application WO 2011/051812 by the Applicant.

As for the first implant 16, the second implant 18 is deformable between a retracted insertion configuration and a deployed configuration implanted in the branch 14 and in the window 26 of the first implant, as shown in FIG. 2. Advantageously, the second implant 18 is auto-expandable.

In the retracted configuration, the second implant 18 has a minimal radial expanse. In the configuration, the radial member 44 is radially contracted near the axis B-B'. The second implant 18 can be conveyed through the central passage 24 and the window 26.

In the deployed configuration, the second tubular body 42 has a maximal radial expanse around the axis B-B'. The radial member 44 is deployed transversely relative to the axis B-B'.

As illustrated by FIGS. 3 to 7, the elastic ring 20 is assembled on the tubular wall 28 of the tubular body 22 around the window 26. The ring 20 delimits a central passage 60 for insertion of the second implant 18, the expanse and contour of which can conform to the expanse and outer contour of the second implant 18.

In the example illustrated in FIGS. 6 to 7, the elastic ring 20 comprises an elastic member formed by a circumferential spring 70 and an envelop 72 defining a housing 74 for receiving the spring 70.

The spring 70 extends around a central axis C-C'. It is for example in the shape of a toroid. Advantageously, the spring 70 is closed on itself. The spring 70 defines a central opening 76.

In the example illustrated in FIG. 7, the spring 70 is a helical spring having a plurality of turns 78 extending substantially radially relative to the central axis C-C'. It is formed with a base of a metal filiform strand wound in a spiral around itself.

The turns of the helical spring 70 define an inner toroid cavity.

Advantageously, the ratio between the diameter of the turns 78 and the diameter of the strand is comprised between 5 and 15, advantageously between 8 and 12, and in particular approximately equal to 10.

Typically, the diameter of the strand is comprised between 0.1 mm and 0.2 mm, and the diameter of each turn 78 is comprised between 0.6 mm and 2 mm.

Likewise, the ratio between the diameter of the central opening 76 and the diameter of each turn 78 is comprised between 8 and 15.

The spring 70 is elastically deformable, radially relative to the axis C-C'.

It is reversibly deformable over a reversible elastic deformation range greater than 20%, advantageously at least 30%. Thus, the perimeter of the spring 70 can increase elastically and reversibly by at least 20%, advantageously at least 30%, which increases the diameter of the central opening 76.

The elasticity modulus of the spring 70, as measured by dynamometry, is for example comprised between 4 N/mm and 8 N/mm.

As illustrated by FIG. 6, the envelop 72 extends around a central axis D-D'. It comprises an outer collar 80, an inner collar 82 and a central tubular wall 84 connecting the inner edges 86 of the collars 80, 82.

The collars 80, 82 and the central wall 84 are advantageously integral. They are for example made from woven or knit cloth, such as a polyethylene terephthalate or polytetrafluoroethylene cloth.

The collar 82 is for example attached by its outer edge 88 on an outer surface of the wall 28 of the tubular body 22. The inner collar 82 is for example attached by its outer edge 88 on an inner surface of the tubular wall 28 around the window 26. The tubular wall 28 is thus partially received in the housing 74 defined between the collars 80, 82.

The central wall 84 extends between the collars 80, 82 from their inner edges 86.

The housing 74 is thus in the shape of an annular groove extending around the axis D-D'. The housing 74 is radially closed off toward the axis D-D' by the central wall 84. It is outwardly closed off by the collar 80 and inwardly by the collar 82.

When the ring 20 is assembled on the tubular wall 28, the housing 74 is radially closed off away from the axis D-D' by the perimeter of the window 26.

The spring 70 is received in the housing 74 between the central wall 84 and the collars 80, 82. It is advantageously positioned bearing against the central wall 84.

The ring 20 thus defines, in the window 26, the insertion passage 60 for the second implant 18, the outer contour and expanse of which are adaptable to the outer contour of the second implant 18. The insertion passage 60 extends axially through the envelop 70, in the central wall 84. The spring 70 is mounted around the passage 60.

Thus, the ring 20 is elastically deformable in the window 26 to allow a reversible increase of at least 20%, advantageously at least 30%, of the outer perimeter of the insertion passage 60.

This reversible deformation in particular results from the presence of the spring 70, which can extend radially and reversibly by separating its turns 78.

Thus, the second implant 18 is movable relative to the first implant 16 between an idle position, situated away from the lateral window 26, and an active position implanted in the lateral window 26.

In the implanted active position, the ring 20 is elastically deformed around the second tubular body 42. The contour of the central passage 60 then has a shape conjugated to the outer contour of the second body 42 in contact with the elastic ring 20.

To guarantee good sealing, the outer contour of the second body 42 in its deployed configuration has an expanse greater than the expanse of the inner contour of the insertion passage 60 without deformation of the spring 70.

When the second implant 18 is received in the insertion passage 60, a radial retaining and sealing force is applied against the outer surface of the second tubular body 42, irrespective of the spatial configuration of the second tubular body 42 relative to the first tubular body 22.

In particular, the sealing is done over the entire periphery of the passage 60.

The ring 20 therefore guarantees sealing creating a significant and continuous force at the interface between the first implant 16 and the second implant 18 in the window 26, the ring 20 forming a continuous lip of the first implant 16 applied on a connection zone of the second implant 18.

Furthermore, the second implant 18 is retained extremely robustly in the first implant 16, since the force necessary for tearing out of the second implant 18 from the ring 20 is greater than 20 N, and is in particular approximately 25 N.

An example method for manufacturing a ring 20 attached on the first implant 16 will now be described.

This method is for example implemented using a device 100 shown in FIG. 8 and FIG. 9.

The device 100 comprises a first mandrel 102 and a second mandrel 104 connected to each other by an intermediate rod 106. The mandrels 102, 104 are mounted on the rod 106 with a given adjustable separation.

In a first embodiment, a tube 109 of flexible material designed to form the envelop 72 is cut. The tube 109 is engaged around the first mandrel 102, the intermediate space 108 between the mandrels, in which the rod 106 is housed, and the second mandrel 104.

Then, a link is made around the tube 109 at the intermediate space 108 to form a throttle 110 in the tube 109.

Then, the device 100 is plunged in a liquid to freeze the deformation of the tube 109 caused by the link. Next, the link is once again tightened, and the distance between the two mandrels 102, 104 is minimized.

The configuration of the tube 109 is then frozen, as previously described. The deformed tube 109 is next dried, and the excess material is cut at the periphery to form the collars 80, 82.

The spring 70 is then engaged in the housing 74 formed by the throttle 110, then the collars 80, 82 are fastened on the tubular wall 22 of the first implant 16.

Then, a tight coating is applied on the envelop 70 to guarantee its liquid-tightness. The tight coating is for example made from silicone impregnating the structure.

In one alternative, the tube 109 is formed by a strip wound around the mandrels 102, 104 across from the intermediate space 108.

The use of the first kit 10 according to the invention will now be described. Initially, the first implant 16 is inserted into the body, for example by the endoluminal route.

To that end, the first implant 16 is loaded in its retracted configuration on a first release device (not shown) and is conveyed to the main segment 12.

Once it is in the main segment 12, the window 26 is positioned across from the branch 14.

The radiopaque nature of the spring 70 is advantageously used to position the window 26 angularly and axially relative to the branch 14.

Once that is done, the first tubular body 22 is deployed to its expanded configuration, to bear against the wall of the main segment 12.

Then, the second implant 18, loaded on a second release device (not shown), is brought to the first implant 16, for example by the endoluminal route.

In a first embodiment, the second implant 18 is conveyed to the main segment 12, then it is inserted into the central passage 24 of the first tubular body 22.

The second release device is then guided on a surgical guide to partially remove the second implant 18 from the first implant 16 through the window 26. To that end, at least part of the second tubular body 42 is engaged through the central passage 60 of the elastic ring 20.

The distal edge of the second implant 18 is maintained in the central passage 24 of the first implant 16.

Then, the second tubular body 42 is placed in its deployed configuration, at least at its proximal end.

The radial member 44 is then radially deployed relative to the tubular body 42 and engages in the central passage 26 across from the elastic ring 20.

The elastic ring 20 being elastically deformable over a wide deformation range, it automatically adapts its inner contour to the outer contour of the second implant 18, irrespective of the spatial configuration and the relative orientation of the second implant 18 relative to the first implant 16.

The sealing is therefore produced safely by the elastic ring 20 attached on the first implant 16, which guarantees that no bodily fluid leak exists between the first implant 16 and the second implant 18.

Then, the distal part of the second implant 18 is deployed in the branch 14 and is pressed against the wall of the branch 14.

In a second implantation mode of the second implant 18, the second implant 18 is inserted through the branch 14 toward the first implant 16, to insert the radial member 44 in the contracted configuration in the central passage 24. Then, the radial member 44 is deployed and is placed abutting against an inner surface of the peripheral wall 28 around the window 26.

Next, the second tubular body 42 is gradually deployed from the radial member 44 toward its distal end.

A second kit 130 according to the invention is illustrated by FIG. 10. Unlike the first kit 10, the first implant 16 of the second kit 130 delimits a plurality of windows 26. It further comprises, for each window 26, a second implant 18 designed to be implanted in the window 26, and an elastic ring 20, attached on the first implant 16 around the window 26.

The kit 130 is for example designed to be implanted in the aortic arch. The different windows 26 are placed across from the three branches 14 present in the aortic arch.

As previously described, the first implant 16 is deployed in the main segment 12, placing each window 26 across from a branch 14. Then, each second implant 18 is implanted through a window 26 to protrude into a branch 14 as previously described.

In light of the significant torsion of the first implant 16 in the main segment 12 and the variable orientations of the branches 14, the presence of an elastic ring 20 around each window 26 guarantees that the sealing is produced around each second implant 18, irrespective of the relative orientation of the second implant 18 relative to the first implant 16 and the initial configuration of the window 26.

Figure 11:
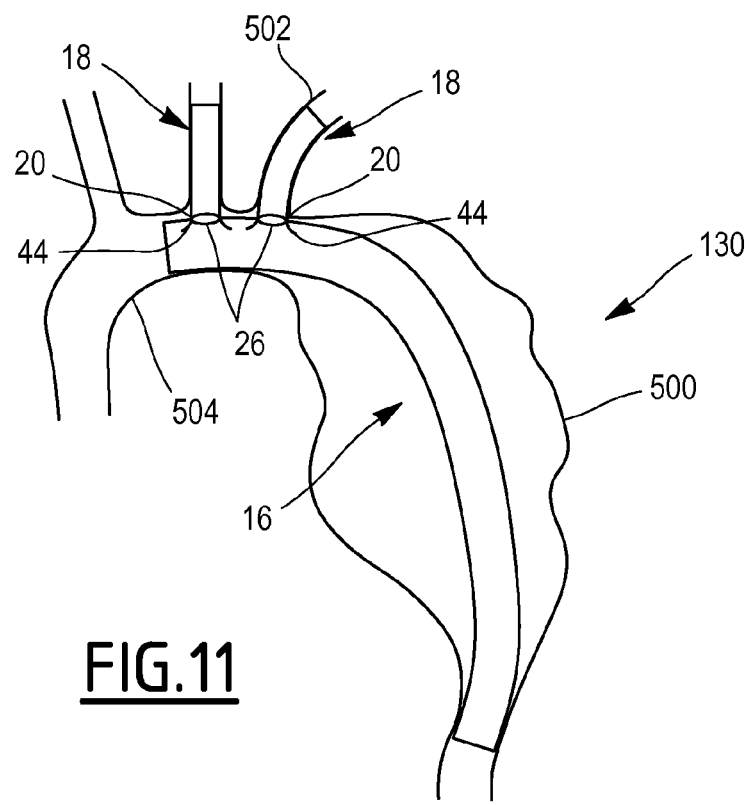
FIG. 11 is a partial sectional diagrammatic view of the second kit according to the invention, implanted in an aneurysm of the descending thoracic aorta requiring covering the left subclavian artery and/or the left common carotid artery.

One application of the second kit 130 according to the invention is illustrated by FIG. 11. One such kit 130 is designed to be implanted in an aneurysm 500 of the descending thoracic aorta needing to cover the left subclavian artery 502 and the left common carotid artery 504 to have a sufficient anchoring neck. In this configuration, the ostia of the vessel is most often adjacent to the window 26.

In that case, the first implant 16 comprises two windows 26 respectively placed across from the left subclavian artery and the common carotid artery. The second implants 18 are inserted from vessels respectively branched through the left subclavian artery and the left common carotid artery up to each window 26.

Then, the radial members 44 of the respective implants 18 are deployed within each elastic ring 20 present around the window 26. The kit 130 thus implanted very effectively blocks any migration of the first implant 16, which is completely immobilized partly in the aortic arch 504 and partly in the aneurysm 500.

Likewise, even if the arteries 502, 504 have varied angles with the local axis of the aortic arch, the sealing between each second implant 18 and the first implant 16 at the windows 26 is guaranteed by the presence of the elastic rings 20. The risk of migration of the first implant 16 is further minimized by the substantial retaining force created by the rings 20.

Figure 12:
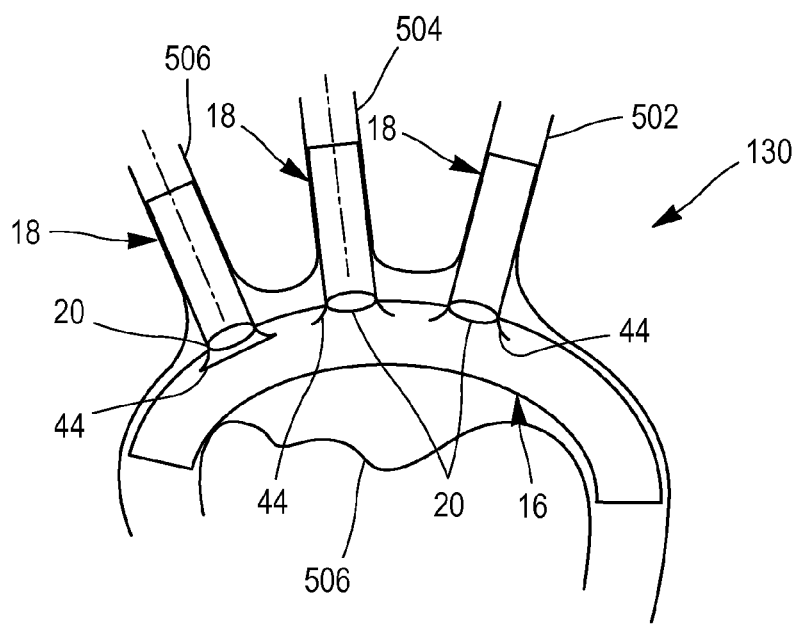
FIG. 12 is a schematic partial sectional view of the second kit according to the invention, implanted in an aneurysm of the aortic arch where the ostia of the supra-aortic trunks are remote from the windows.

Another application of the second kit 130 according to the invention is illustrated by FIG. 12. In this application, the first implant 16 is implanted through an aneurysm 506 of the aortic arch 504 in which the ostia of the super-aortic trunks 502, 504, 508 are remote from the windows 26 provided in the first implant 16.

The second implants 18 are inserted through the trunks 502, 504, 508 and exert traction on the first implant 16 by means of the elastic rings 20 cooperating with the retaining members 44 of each second implant 18.

Thus, the second implants 18 cause the first implant 16 to rise in the aortic arch 504 to hug the largest curve thereof and reduce the migration and leak risk at the necks. In fact, the axes of the necks are aligned with the implant 18.

Figure 13:
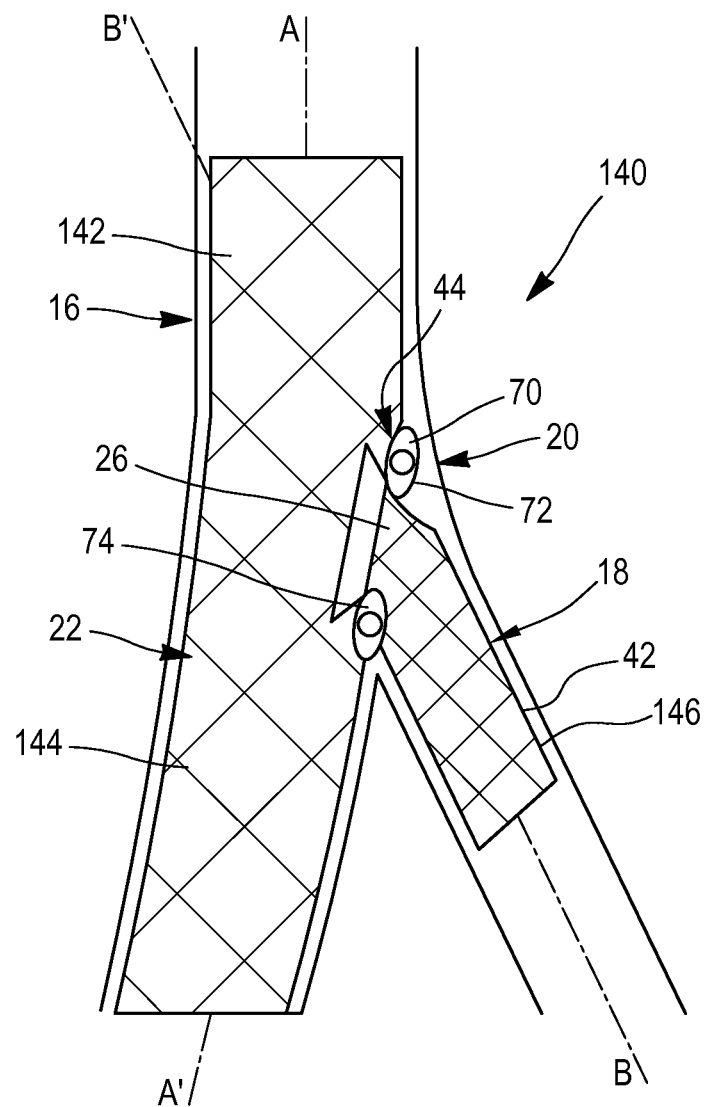
FIG. 13 is a partial sectional view of a third kit according to the invention, once implanted in a Y-shaped blood flow conduit.

A third kit 140 according to the invention is illustrated by FIG. 13. This kit 140 comprises a first implant 16 having a main trunk 142 and a first leg 144. The implant 16 delimits a window 26 at the base of the trunk, situated opposite the first leg 144. The second implant 18 is designed to be implanted in the window 26 to form a second leg 146.

The kit 140 thus forms a generally Y-shaped bifurcated prosthesis.

In this example, the angle formed between the local axis A-A' of the first implant 16 at the window 26 and the axis B-B' of the second implant 18 is less than 90° and is in particular comprised between 30° and 45°.

The radial member 44 in its deployed position is further situated in a plane that is inclined relative to the local axis B-B' of the second implant 18. Owing to the elastic ring 20 present on the first implant around the window 26, the sealing around the second implant 18 is therefore ensured very effectively.

Figure 14:
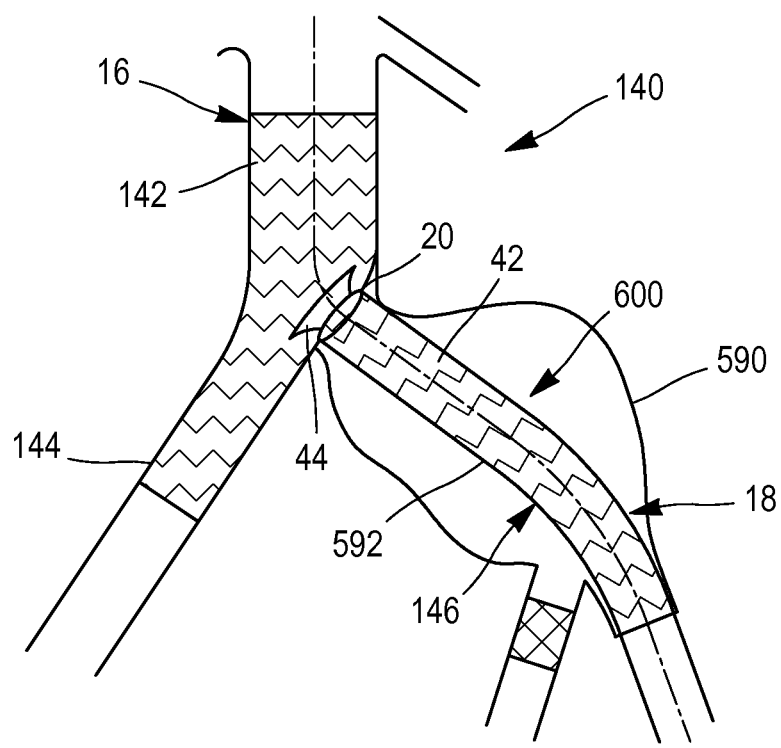
FIG. 14 illustrates the third kit according to the invention, implanted in a unilateral iliac aneurysm with no proximal neck.

One application of the third kit 140 according to the invention is shown in FIG. 14. In this application, the third kit 140 is for example designed to treat an aneurysm 590 of the common iliac artery 592 in a patient with no associated aortic aneurysm and without a proximal neck making it possible to place a tubular endoprosthesis in the iliac artery 592.

In that case, the main trunk 142 advantageously has a diameter comprised between 15 mm and 25 mm, and a height comprised between 2 cm and 3 cm so as not to cover the origin of the superior mesenteric artery.

The branch 146 has a diameter comprised between 8 mm and 14 mm, and a length comprised between 2 cm and 3 cm.

The fourth kit according to the invention 140 therefore makes it possible to produce branches 146 with pre-established angulations, which is very advantageous in clinical practice.

In this configuration, the proximal endoprosthesis comprises a proximal part adapting to the diameter of the patient's aorta and a distal part adapting to the diameter of his proximal iliac artery, the proximal part and the distal part being in a single piece. The length of the proximal (aortic) and/or distal (iliac) parts may be adapted to avoid covering the inferior mesenteric artery and/or the inner iliac artery.

In one alternative, the outer surface of the second tubular body 42 of the second implant 18 is provided with an adhesive coating, for example made from silicone at its contact zone with the ring 20.

The adhesive coating favors the fastening of the second implant 18 in the ring 20 in contact with the envelop 72.

In one alternative, the envelop 72 of the elastic ring 20 is covered with a tight coating, which is advantageously biodegradable. That coating is for example formed by PLA nanofibers, which plug the orifices of the cloth forming the envelop 72.

Figure 15:
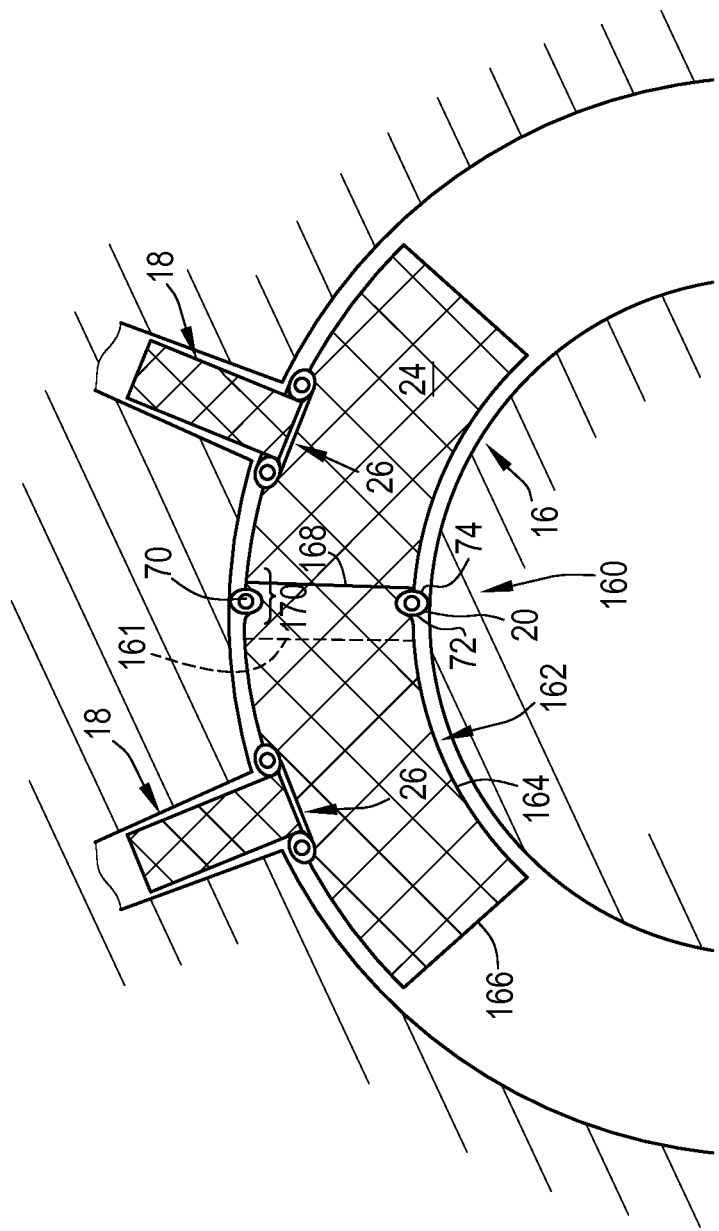
FIG. 15 is a partial sectional view of a fourth kit according to the invention.

A fourth kit 160 according to the invention is illustrated by FIG. 15. Unlike the first kit 10, the first implant 16 defines an axial window 161 in which a third implant 162 is inserted. The axial window 161 extends at one axial end of the first implant 16 and is formed by an axial opening emerging in the central passage 24.

The first implant 16 comprises an additional retaining ring 20 extending around the axial window 161. The additional retaining ring 20 is elastically deformable in the window 161 to allow a reversible increase of at least 20%, advantageously at least 30% of the outer contour of the insertion passage of the third implant 161 defined by the additional retaining ring 20.

The additional retaining ring 20 is advantageously of the type described above. It comprises a circumferential spring 70 and an envelop 72 delimiting a housing 74 for receiving the spring 70.

The third implant 162 is designed to be inserted through the window 161. It has a third tubular body 164 extending between a first axial edge 166 and a second axial edge 168. An axial end segment 170 of the third implant 162 is inserted through the central passage 24 of the first implant 16 through the window 161.

As previously described, the retaining ring 20 deforms around the outer surface of the third tubular body 164 to produce sealing around that surface. Thus, the inner contour of the ring 20 has a shape conjugated to that of the outer contour of the axial segment 170 of the third implant 162 positioned in the first implant 16.

Advantageously, the first implant 16 and the third implant 164 each delimit a lateral window 26 receiving a second implant 18.

The presence of a third implant 162 that is axially movable in a first implant 16, and sealably retained by a retaining ring 20 according to the invention, therefore makes it possible to adjust the relative axial position of the second implants 18 with respect to one another, to adapt to different anatomical configurations.

Thus, it is not necessary to directly provide, in the first implant 16, several insertion windows 26 for a second implant 18 axially spaced away from one another by a predetermined distance that must be provided when the implant 16 is designed.

It is, on the contrary, possible to standardize the position of the windows 26 on each implant 16, 162, then first to implant the first implant 16, and next axially insert the third implant 162 into the first implant 16 in order to place the window 26 of the third implant 162 at the selected distance to be situated across from the specific anatomical conduit of the user.

Figure 16:
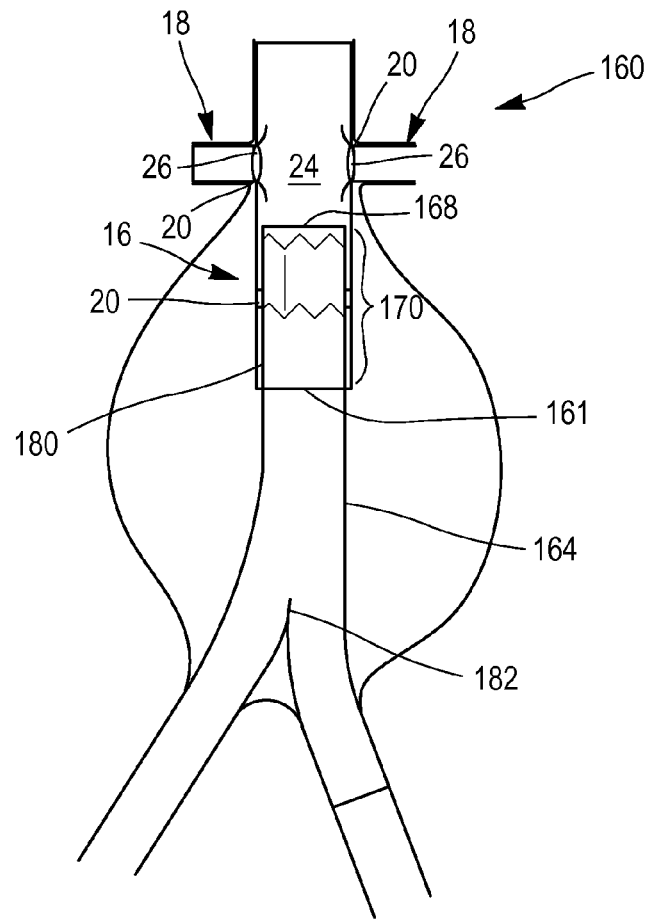
FIG. 16 illustrates an alternative of the fourth kit according to the invention.
Figure 17:
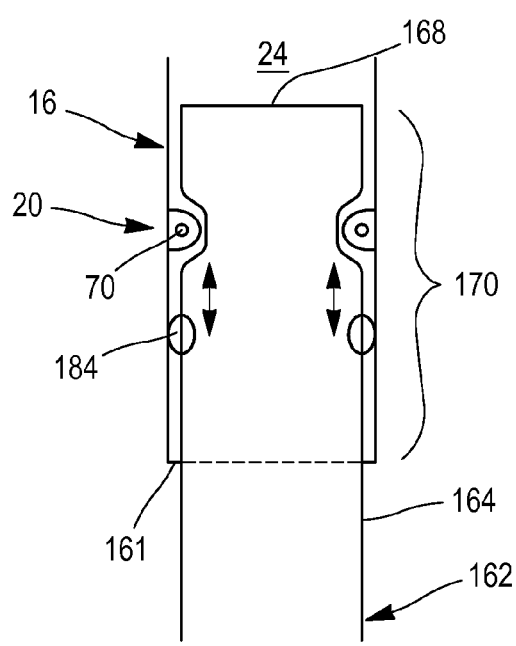
FIG. 17 illustrates a detail of the alternative of FIG. 16.

One example application of the fourth kit 160 according to the invention is illustrated by FIGS. 16 and 17.

In this example, the first implant 16 is positioned in a linear part of the subrenal aorta and in the abdominal aorta. The second implants 18 are positioned in the renal arteries through windows 26 provided with elastic rings 20 as described above.

The third implant 162 has a common trunk 180 partially inserted into the axial window 161 of the first implant 16 and a bifurcation 182 comprising legs inserted into the iliac arteries.

An additional elastic ring 20 is positioned in the first implant 16 around the axial window 161. The ring 20 deforms around the outer surface of the third tubular body 164 to produce sealing around that surface. Thus, the inner contour of the ring 20 has a shape conjugated to that of the outer contour of the axial segment 170 of the third implant 162 positioned in the first implant 16.

As illustrated in FIG. 17, the additional ring 20 radially deforms the axial segment 170 toward the axial segment, ensuring axial retaining of the third implant 162 relative to the first implant 16.

This connection, due to its elastic properties, adapts to the movements imposed by the systolic flow. The connection therefore acts as a damper that allows the downstream segment of the third implant 162, which comprises the bifurcation, to be subject to micro-movements imposed by the drag forces without passing those forces on to the zones that comprise the branches 18 and the windows 26 in the renal arteries and avoid the risk of separations.

In one alternative, shown in dotted lines in FIG. 17, a pad 184 is positioned around the axial segment 170 of the third implant 162. The pad 184 moves between the axial window 161 and the additional ring 20 when the axial segment 170 of the third implant 162 is inserted into the first implant 16.

Examples of second implants 18 designed to be inserted into a window 26 of the first implant 16 will now be described in FIGS. 18 to 22.

In a first example implant 18, shown in FIGS. 18 to 20, the tubular body 42 of the implant 18 comprises an openworked tubular frame 50 and an outer layer 52 fastened around the frame 50. The outer layer 52 has a part 590 fastened on the frame 50 and a flare 600 that protrudes radially and axially away from the frame 50.

The radial retaining member 44 is fastened on the flare 600. In this example, it comprises a plurality of retaining fingers 602 protruding radially.

The second implant 18, in its retracted configuration, is for example inserted into the window 26 of a first implant 16 (see FIG. 20), through a lateral branch of the vessel in which the first implant 16 is positioned.

Once inserted into the central passage 24, the radial retaining member 44 is first deployed, then wedged against the inner surface of the first tubular body 22 across from the retaining ring 20.

Next, the second tubular body 42 is deployed and pressed against the retaining ring 20. The latter then elastically deforms to hug the shape and angular orientation of the second implant 18.

FIGS. 21 and 22 illustrate an alternative second implant 18 for a kit according to the invention.

In this alternative, the radial retaining member 44 is secured to the frame 50. It is in particular integral with the frame 50.

As illustrated by FIG. 21, the radial retaining member 44 is for example formed by a frustoconical skirt protruding radially from the tubular frame 50. The skirt 610 is axially folded across from the tubular frame 50. The flare 600 is fastened on the skirt 610.

Furthermore, the implant described in FIG. 21 can be placed in a release launcher in the configuration described in this FIG. 21 and may be released using the fixed-point withdrawal principle. This has the drawback of doubling the stent and membrane thicknesses. To offset this problem, the implant 18 may be positioned in the launcher not with the skirt 610 folded on the frame 50, but with the skirt 610 extended by using a specific launcher. This launcher comprises a retractable stop on which the frame 50 is pushed to allow the flaring of the skirt 610. Next, the stop is retracted and the rest of the frame 18 is released using the fixed-point withdrawal principle.

During the placement of the implant 18 in the window 26, the skirt 610 is wedged below the ring 20 while pressing on the inner surface of the tubular body 22.

Advantageously, the second implant 18 further comprises wedging tabs 612 for the retaining member 44, shown in FIG. 22. The tabs 612 protrude from the outer surface of the second body 42 toward the retaining member 44, across from the latter.

The wedging tabs 612 and the retaining member 44 thus delimit an intermediate space 612 for wedging the ring 20.

When the second implant 18 is placed in the window 26, the ring 20 is gripped between the tabs 612 positioned on the outer collar 80 and the retaining member 44 pressed on the inner collar 82.

The retaining of the second implant 18 relative to the first implant 16 is therefore very robust.

In the invention described above, the retaining ring 20 is elastically deformable in the window 26 to allow a reversible increase of at least 20% of the outer contour of the insertion passage 60.

This constitutes a difference relative to the device of the state of the art, in which the retaining ring is not very deformable, for example with a deformability of less than 10%, and in which a second implant deployed by an inflatable balloon must be used to offset any retraction of the second implant, after the balloon is deflated.

The presence of a reversible elastic deformation of at least 20% of the outer contour of the insertion passage makes it possible to accommodate auto-expandable implants 18, and guarantee sealing around the second implant 18, irrespective of the orientation or configuration of the second implant 18. A joining system for two mechanically opposing elastic structures is thus created making it possible not only to generate a very significant joining force, but also a geometric adaptation of the joining. This is not the case if we place a collar with a low deformation power as in the state of the art.

The sealing is further improved by the retaining member 44 of the second implant 18, in particular when that member 14 is a collar, that collar being able to cooperate with the retaining ring 20. When the retaining ring 20 is provided on its outer surface with a sealing coating, and optionally an adhesive coating, in particular made from silicone, the sealing is further improved.

In one preferred embodiment of the invention, the retaining ring comprises an envelop 72 formed by a first collar 80 fastened on an outer surface of the first body 22, a second collar 82 fastened on an inner surface of the first body 22 and a circumferential wall 84 connecting the first collar to the second collar 82.

Preferably, the collars 80, 82 and the circumferential wall 84 are integral.

The envelop 72 attached on the first tubular body 22 of the first implant 16 considerably simplifies the manufacture of the treatment kit according to the invention, relative to the kits described in the state of the art. In particular, the specific configuration of the collar, with an outwardly open toroid profile forming a radial gutter, makes it possible to house the elastic member 70 present in the retaining ring 20 safely, while guaranteeing the deformability of the ring 20 in the claimed range.

The envelop 72 being preformed in this configuration and attached in the window 26, the stresses applied on the wall of the first implant 16 are minimal, which guarantees the solidity of the implant 16 around the window 26.

The retaining ring 20 is also particularly simple to place industrially.

This is a major advantage relative to the solutions in which an eversion of the wall of the implant is done to form a retaining ring. These solutions in fact have the drawback of being difficult to carry out industrially, inducing major stresses on the body of the implant, and opposing the free deformation of the retaining ring.

In one advantageous alternative, an extension limiter, for example formed by a rigid wire that is not elastically deformable, is inserted into the retaining ring 20 to limit the reversible increase of the outer contour of the insertion passage 60.

The limiter is for example inserted into the elastic member 70, for example at the center 70a of the spring. The maximal elastic deformation of the retaining ring 20 is then limited, which still guarantees use of the elastic member 70 in its reversible deformability range.

The invention claimed is:

1. A treatment kit, comprising:
   a first implant, the first implant comprising a first tubular body, an outer surface thereof having a void therein that defines a window;
   a second implant comprising a second tubular body positionable within the window of the first tubular body so as to protrude relative to the first implant, the second implant further comprising a retaining member configured to retain the second implant relative to the first implant; and
   a retaining ring that retains the second implant, said retaining ring provided on the first tubular body in the window and delimiting an insertion passage for the second implant, the retaining ring being elastic so as to be elastically deformable in the window such to permit the insertion passage to reversibly increase by at least 20%,
   wherein the retaining ring comprises first and second annular collars, each defined by an outer perimeter, an inner perimeter, and a central void delimited by the inner perimeter, and a connecting portion that extends laterally from the inner perimeter of the first collar to an inner perimeter of the second collar to form the insertion passage, a length of the connecting portion spacing the first collar from the second collar, a space extending radially from an outward-facing surface of the connecting portion, and between opposing inward-facing radial surfaces of the first and second collars, defining a housing that extends at least partially around the window, and
   wherein an elastic member is positioned inside the housing, and
   wherein a portion that surrounds the window of the first tubular body is received within the housing, a radial surface of the first collar fastened on the outer surface of the first tubular body, and an opposite-facing radial surface of the second collar fastened on an inner surface of the first tubular body.

2. The kit according to claim 1, wherein the second implant is movable relative to the first implant between an idle position spaced away from the window and an active position implanted in the window, the retaining ring being elastically deformed when the second tubular body is positioned in the window, an inner contour of the insertion passage having a shape conjugated with an outer contour of the second tubular body situated in contact with the retaining ring.

3. The kit according to claim 1, wherein the elastic member is a helical spring.

4. The kit according to claim 1, wherein the first collar, the second collar and the connecting portion are integral.

5. The kit according to claim 1, wherein the retaining member of the second implant is formed by a radial deployable collar.

6. The kit according to claim 1, wherein the second implant is auto-expandable between a retracted configuration and a deployed configuration.

7. The kit according to claim 1, wherein the first tubular body is a tubular endoprosthesis, and the second tubular body is a tubular endoprosthesis.

8. The kit according to claim 1, wherein the first tubular body delimits a central passage extending along a longitudinal axis between a first axial opening and a second axial opening, the window being a lateral window emerging transversely relative to the longitudinal axis between the axial openings.

9. The kit according to claim 1, wherein the retaining ring comprises an extension limiter.

10. The kit according to claim 1, wherein the retaining ring is elastically deformable in the window to allow a reversible increase of at least 30% of the insertion passage.

11. A treatment device, comprising:
    a first implant comprising a first tubular body, an outer surface thereof having a void therein that defines a window; and
    a retaining ring configured to retain a second implant, assembled to the window and delimiting an insertion passage for the second implant,
    wherein the retaining ring is elastically deformable in the window such to permit a reversible increase, of at least 20%, of the insertion passage,
    wherein the retaining ring comprises first and second annular collars, each defined by an outer perimeter, an inner perimeter, and a central void delimited by the inner perimeter, and a connecting portion that extends laterally from the inner perimeter of the first collar to an inner perimeter of the second collar to form the insertion passage, a length of the connecting portion spacing the first collar from the second collar, a space extending radially from an outward-facing surface of the connecting portion, and between opposing inward-facing radial surfaces of the first and second collars, and
    wherein an elastic member is positioned inside the housing, and
    wherein a portion of the first tubular body that surrounds the window is received within the housing, a radial surface of the first collar fastened on the outer surface of the first tubular body, and an opposite-facing radial surface of the second collar fastened on an inner surface of the first tubular body.

12. The treatment device according to claim 11, wherein the retaining ring is elastically deformable in the window to allow a reversible increase of at least 30% of the outer contour of the insertion passage.

13. A method for manufacturing a treatment device with a first implant comprising a first tubular body that includes a window where an end of a second implant attaches, the method comprising the following steps:
providing the first implant; and
fastening a retaining ring for retaining the second implant into the window of the first implant, the retaining ring delimiting an insertion passage for the second implant, said fastening of the retaining ring including the sub-steps of:
providing the retaining ring as an assembly of first and second annular collars, defined by an outer perimeter, an inner perimeter, a central void delimited by the inner perimeter, and a connecting portion that extends laterally from the inner perimeter of the first collar to an inner perimeter of the second collar to form the insertion passage,
a space extending radially from an outward-facing surface of the connecting portion, and between opposing inward-facing radial surfaces of the first and second collars, delimiting housing;
placing an elastic member into the housing; and
receiving portions of the first tubular body located at the window inside the housing.

14. The method according to claim 13, wherein the sub-steps further include fastening the first annular collar on an outer surface of the first tubular body, and fastening the second annular collar on an inner surface of the first tubular body.

15. The method according to claim 13, further comprising:
a step for manufacturing the retaining ring, including
forming a tube;
creating a throttle in the tube; and
freezing the throttle in the tube to form the housing.

* * * * *